Figure 1:
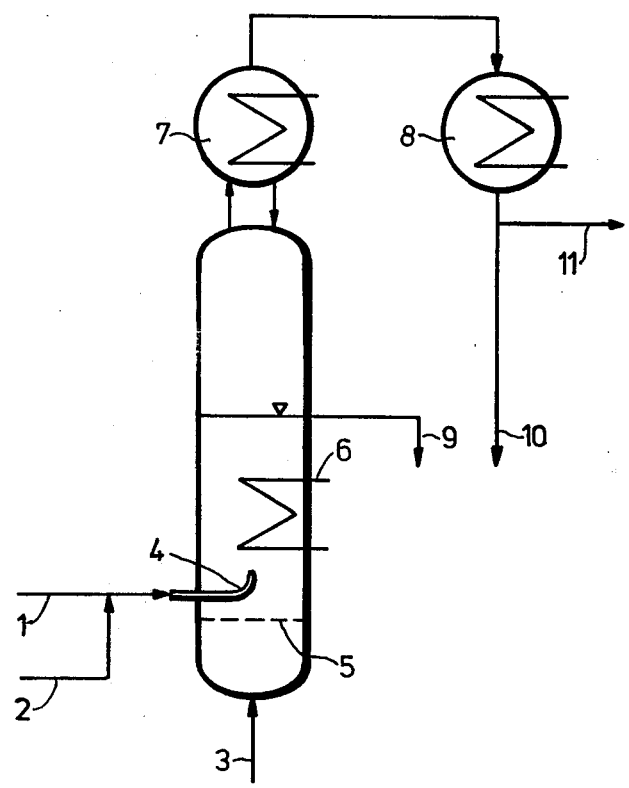

United States Patent [19]

Lenthe et al.

[11] 4,216,332
[45] Aug. 5, 1980

[54] PREPARATION OF CHLORINATED N-METHYL-IMIDAZOLES AND N-METHYL-IMIDAZOLINES

[75] Inventors: Manfred Lenthe, Odenthal-Neschen; Gerhard Dankert, Cologne, both of Fed. Rep. of Germany

[73] Assignee: Bayer Aktiengesellschaft, Leverkusen, Fed. Rep. of Germany

[21] Appl. No.: 974,411

[22] Filed: Dec. 29, 1978

[30] Foreign Application Priority Data

Jan. 25, 1978 [DE] Fed. Rep. of Germany ....... 2803037

[51] Int. Cl.$^2$ ................... C07D 233/28; C07D 233/68
[52] U.S. Cl. ............................... 548/337; 260/566 D; 548/351
[58] Field of Search ............................ 548/337, 351; 260/566 D

[56] References Cited

U.S. PATENT DOCUMENTS 3,631,058   12/1971   Beck et al. ........................... 548/337

FOREIGN PATENT DOCUMENTS 1221212   7/1966   Fed. Rep. of Germany .
1670913   3/1971   Fed. Rep. of Germany .

OTHER PUBLICATIONS

Beck et al. Angew. Chem. 1974, vol. 86, p. 134.
Beck et al. Angew. Chem. International Edition in English 1974, vol. 13, p. 210.

*Primary Examiner*—Natalie Trousof

*Attorney, Agent, or Firm*—Sprung, Felfe, Horn, Lynch & Kramer

[57] ABSTRACT

In the preparation of chlorinated N-methyl-imidazoles and N-methyl-imidazolines of the formula

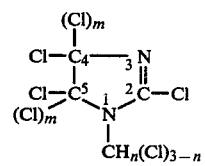

in which
n represents the number 0, 1, 2 or 3 and
m represents the number 0 or 1, a double bond being present between the C atoms in the 4-position and 5-position when m is 0, and a single bond being present when m is 1, by chlorinating N,N-dimethylaminoacetonitrile of the formula

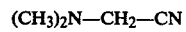

or its hydrochloride, the improvement which comprises introducing aminoacetonitrile or its hydrochloride into a mixture of its chlorination products, with simultaneous addition of chlorine gas, in the absence of a solvent, at a temperature from about 70° to 150° C. The product can be further chlorinated at 130° to 220° C. to produce tetrachloro-ethylene-bis-isocyanide dichloride.

4 Claims, 2 Drawing Figures

PREPARATION OF CHLORINATED N-METHYL-IMIDAZOLES AND N-METHYL-IMIDAZOLINES

The present invention relates to an unobvious process for the preparation of known chlorinated N-methyl-imidazoles and -imidazolines, which are used as intermediate products for the synthesis of tetrachloroethylene-bis-isocyanide dichloride; the latter compound can be used for the production of pesticidally active compounds.

It has already been disclosed that chlorination of N,N-dimethylamino-acetonitrile gives tetrachloroethylene-bis-isocyanide dichloride; the synthesis route is via chlorinated N-methyl-imidazoles and -imidazolines (see, in this context, DT-AS (German Published Specification) 1,221,212 and DT-OS (German Published Specification) 1,670,913, as well as Angew. Chem. 86, 134 (1974)). As stated in detail (see the above-mentioned DT-OS (German Published Specification) 1,670,913), N,N-dimethylaminoacetonitrile is, for this purpose, introduced into a chlorinated aliphatic hydrocarbon as the solvent and is chlorinated at temperatures of up to 150° C., if appropriate while irradiating with ultraviolet light. For the synthesis of the various chlorinated N-methyl-imidazoles and -imidazolines specified later, temperature programs are prescribed and, if these are observed, the compounds are synthesized in yields of at most 68% of theory.

All processes in which solvents are used for the chlorination of the N,N-dimethylaminoacetonitrile have the disadvantage that the solvents must be distilled off, and this entails a high expenditure of energy. Furthermore, the high proportions of solvent reduce the space-time yield of the reaction. Since, furthermore, in the known processes a suspension of N,N-dimethylaminoacetonitrile hydrochloride in the solvent is first produced, further difficulties arise from the treatment of this suspension, which also frequently leads to black, tar-like products. These disadvantages result in high costs of preparation of the products and thus prevent economic utilization of the reaction.

It has now been found that the known chlorinated N-methyl-imidazoles and N-methyl-imidazolines of the general formula

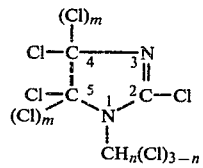

in which
n represents the number 0, 1, 2 or 3 and
m represents the number 0 or 1, a double bond being present between the C atoms in the 4-position and 5-position in the case where m is 0, and a single bond being present in the case where m is 1,
can be obtained in high yield by chlorinating N,N-dimethylamino-acetonitrile of the formula $$(CH_3)_2N-CH_2-CN \qquad (II)$$

or its hydrochloride, if N,N-dimethylaminoacetonitrile or its hydrochloride is introduced into a mixture of its chlorination products, with simultaneous addition of chlorine gas, in the absence of a solvent, at a temperature between about 70° and 150° C.

The N-methyl-imidazoles or -imidazolines obtained in the process according to the invention may be further processed by subjecting them to a high temperature chlorination at a temperature range of between about 130° and 220° C., resulting in the desired secondary product tetrachloroethylene-bis-isocyanide dichloride of the formula $$Cl_2C=N-(CCl_2)_2-N=CCl_2 \qquad (III).$$

It is surprising that in the method according to the invention the chlorinated N-methyl-imidazoles and -imidazolines can be formed in such high yields that the secondary product of the formula (III) is obtained in a yield of 90%, relative to the nitrile of the formula (II) employed. The purity of the secondary product of the formula (III) may be 95 to 99%.

It is an advantage of the process according to the invention that if no solvent is used, the reaction can be conducted in such a way that it does not result in a suspension of the dimethylaminoacetonitrile hydrochloride in the product mixture. This advantage is of importance because, as a result, the gas-solid reaction between the hydrochloride and chlorine, which in the case of the solvent processes can only be prevented with difficulty, and which has obvious disadvantages, can be avoided.

N,N-Dimethylaminoacetonitrile of the formula (II), to be used as the starting material, is a compound which has been known for a long time. It is prepared from dimethylamine, hydrocyanic acid and formaldehyde; such reactions are generally known by the name of "Mannich reactions" (see, in this context, J. Am. Chem. Soc. 68, 1607 (1946) and Liebigs Ann. Chem. 279, 43 (1894)).

The reaction temperatures required for the reaction are illustrated in the section dealing with the examples hereinbelow. In general, the reaction is carried out between about 70° and 150° C., preferably between about 90° and 130° C.

The chlorinated N-methyl-imidazoles and -imidazolines of the formula (I) obtainable in accordance with the invention include, specifically, the following compounds:

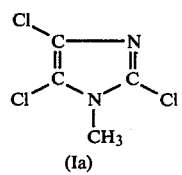
(Ia)

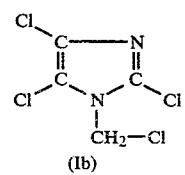
(Ib)

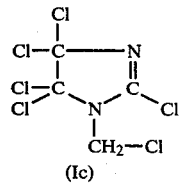
(Ic)

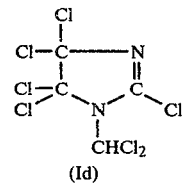
(Id)

The compounds are not, in general, isolated; instead, as already mentioned, the mixture of the chlorinated N-methyl-imidazoles or -imidazolines is subjected to a secondary reaction (chlorination at a high temperature), whereby the compound of the formula (III) is obtained. The last-mentioned compound serves as an intermediate product for the preparation of pesticidally active compounds.

With hydrogen fluoride, the compound (III) gives N,N'-bis-(trifluoromethyl)-tetrafluoroethylenediamine; the latter then gives perfluoro-2,5-diazahexa-2,4-diene, with elimination of 2 mols of hydrogen fluoride, by means of sodium fluoride (see, in this context, DT-AS (German Published Specification) 2,013,433 or U.S. Pat. No. 3,694,507; the compound is obtained by a different method, and is described, by P. H. Ogden and R. A. Mitsch, J. Ann. Chem. Soc. 89, 5008 (1967)). This perfluoro compound, undergoes, for example, a cyclization reaction with N-methyl-N'-(4-chlorophenyl)-thiourea to give the plant protection fungicide 2-methylimino-3-(4'-chlorophenyl)-4,5-bis-(trifluoromethylimino)-thiazolidine, known from the literature (see DT-OS (German Published Specification) 2,062,348 or U.S. Pat. No. 3,895,020).

GENERAL DESCRIPTION OF THE PROCESS

In a stirred kettle reactor (or the first kettle of a stirred kettle cascade) or a bubble column chamber (single stage or multistage), equipped with a heat exchanger for complete condensation of the vapors, dimethylaminoacetonitrile is introduced into a mixture of chlorinated N-methyl-imidazoles and -imidazolines, with simultaneous addition of chlorine via a gas distributor, in such a way that a clear, pale yellow solution can be withdrawn from the reaction space through an outlet.

The speed of addition of the nitrile depends on the temperature: at 90° C., about 70 g of nitrile per liter of reaction volume and per hour can be introduced into a bubble column chamber, and at 130° C. as much as about 120 g of nitrile per liter and per hour, without resulting in the formation of a suspension. The stated values depend on the addition of chlorine: the chlorine is employed in excess, and in particular the molar ratio of nitrile of the formula (II) to chlorine is preferably about 1:5 at 90° C. and preferably about 1:6 at 130° C. These values correspond to the experience that at higher temperature the chlorination leads to the formation of more highly chlorinated N-methyl-imidazoles or -imidazolines.

The reaction can be carried out discontinuously or, to advantage, continuously. In both cases the same reaction apparatuses can be used, with the difference that in the continuous steady state, the reaction volume is kept constant while in the discontinuous, non-steady state method of operation the reaction volume increases progressively so that, due to the constant space-time yield, the overall reaction rate is also increased progressively.

It is very particularly advantageous to use bubble columns, operated continuously or discontinuously, in cocurrent or counter-current, in one or more stages, the chamber or chambers of the columns being equipped with heat exchangers in the form of jackets or of tube coils immersed in the liquid. These apparatuses make it possible to achieve high rates of material exchange between the gas phase and the liquid phase, and to achieve good heat transfer coefficients which, particularly at a high temperature level, make it possible to remove the substantial heat of reaction.

When using a bubble column chamber, the introduction of nitrile, relative to the reaction volume, can be approximately doubled compared to a stirred kettle, without resulting in the formation of a suspension.

To prepare the secondary product (tetrachloroethylene-bis-isocyanide dichloride of the formula (III)), the reaction mixture from the first stage of the process is generally introduced into a stirred kettle or a bubble column and is reacted with chlorine at temperatures from about 130° to 220° C. After 10 to 15 hours, the reaction has ended and the reaction product—fused tetrachloroethylene-bis-isocyanide dichloride—is discharged from the reactor through a suitable device, for example a crystallizing screw. Another possible way of isolating the product is, for example, to take up the hot reaction melt in a solvent in which the compound is only sparingly soluble, for example carbon tetrachloride, chlorobenzene, 1,2-dichloro-benzene or the like, and to filter off the product. In this way, a purification effect is additionally achieved, and the tetrachloroethylene-bis-isocyanide dichloride is obtained as a white mass of crystals, having a melting point of 167° C. (value in the literature: 166° C.).

Figure 2:
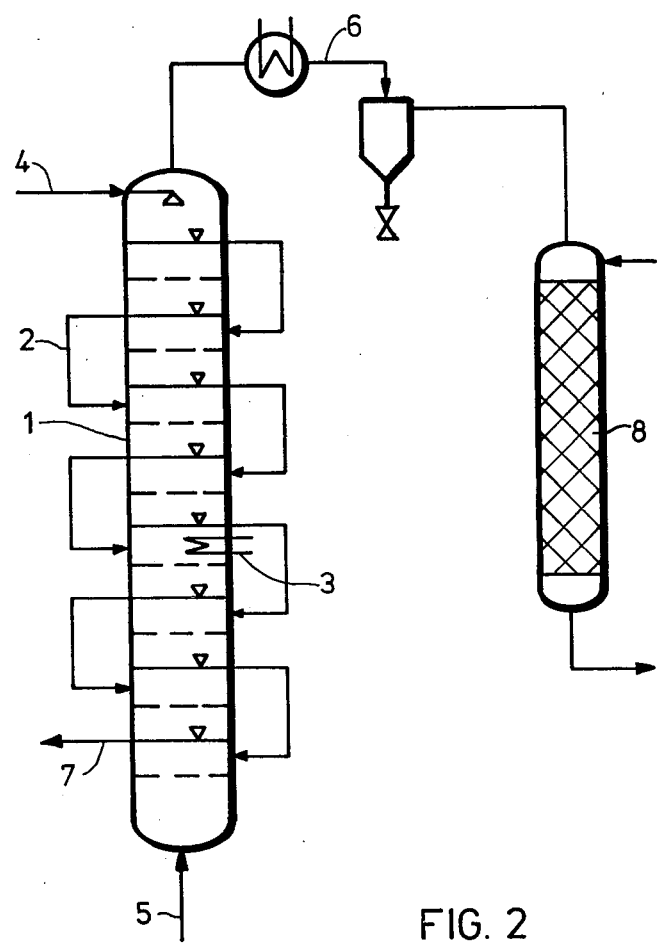

The invention will be further described with reference to the accompanying drawings wherein:

FIG. 1 is a schematic view of an apparatus for carrying out a first stage chlorination; and FIG. 2 is a schematic view of an apparatus for further chlorinating the product from FIG. 1.

Referring now more particularly to FIG. 1, chlorine (3) is introduced via a gas distributor plate (5) into the effervescent layer of material, equipped with a heat exchanger (6). N,N-Dimethylaminoacetonitrile (1) is pumped in through a capillary (4) flushed with nitrogen (2). The product can be drained off via an overflow (9). The vapors produced at higher temperatures are very largely condensed in the reflux condenser (7), while such material as breaks through is condensed in the product condenser (8) and taken off at (10) to ensure material balance. The gases (11) which leave the apparatus are freed from chlorine in an absorber and washed with water to remove the hydrogen chloride.

The chamber has the following dimensions:
Nominal width: 100 mm
Height of the effervescent layer: 500 mm
Volume of liquid: 3.0 to 3.5 liters depending on the gassing conditions.

The products obtained in this stage are stabilized by flushing out the chlorine and are worked up in the next stage (high temperature chlorination) to give tetrachloroethylene-bis-isocyanide dichloride. However, this stabilization is not necessary if the product is worked up directly to give the secondary product.

The apparatus represented in FIG. 2 is used in the Examples for the high temperature chlorination. This apparatus is an eight-stage counter-current bubble column with heat exchangers (23) built into each individual chamber (21). The chlorinated imidazoles/imidazolines are introduced at the top of the column (24) and run, counter-current to the gas (25) downwards via overflows (22) into the sump of the column, from which the finished product is taken off (27). The gases (26) which issue at the top of the column are first partially condensed (reflux condenser) and are taken up in an absorber (28).

EXAMPLE 1

3,000 g of a mixture of chloroimidazoles and chloroimidazolines were introduced into the apparatus of FIG. 1, while gassing the chamber with nitrogen in order to prevent the liquid from running through.

After heating up to 90° C. internal temperature and replacing the nitrogen by 2,500 g/hr of chlorine, 150 g/hr of N,N-dimethylaminoacetonitrile were pumped in through the capillary (4), while at the same time flushing the capillary with nitrogen. The pale yellow product which issued after reaching the overflow (9) was flushed with nitrogen for two hours at room temperature to remove the dissolved chlorine; the product consisted of chlorinated N-methyl-imidazolines and -imidazoles.

Secondary stage:

2,219 g of the resulting mixture of chlorinated N-methyl-imidazoles and -imidazolines were gassed with 1,200 g/hr of chlorine in the same installation and in the course thereof were heated in accordance with the following program:

| Time/hr | Temperature/°C. |
|---|---|
| 5 | 120 |
| 5 | 140 |
| 5 | 160 |
| 5 | 180 |
| 10 | 200 |

2,135 g of product (without distillate) were obtained, containing 95% of tetrachloroethylene-bis-iscocyanide dichloride (III) and 5% of trichloromethyl-isocyanide dichloride (by-product).

EXAMPLE 2

Secondary stage:

2,285 g of the mixture prepared in accordance with the process described in Example 1 and consisting of chlorinated N-methyl-imidazoles and -imidazolines were gassed discontinuously with 1,200 g/hr of chlorine in the bubble column chamber of FIG. 1, in accordance with the following temperature program:

| Time/hr | Temperature/°C. |
|---|---|
| 10 | 120 |
| 10 | 180 |
| 7 | 200 |

2,452 g of product containing 89% of compound (III) and a small proportion of trichloromethyl-isocyanide dichloride were obtained.

EXAMPLE 3

(The preliminary stage according to the invention, and the secondary stage, are in this case combined).

The counter-current bubble column shown in FIG. 2 was modified so that the two uppermost chambers were combined into a larger chamber. The result of this was that at a constant space-time yield the rate of conversion was virtually doubled.

In the first, upper chamber of this column N,N-dimethylaminoacetonitrile was fed, as in the preceding examples, into an initially introduced mixture consisting of chlorinated N-methyl-imidazoles and -imidazolines, at a rate of 140 g/hr, and was reacted with a stream of 1,500 g/hr of chlorine gas. The chambers of the column were run with the following temperature programs:

| Chamber No. | Temperature /°C. |
|---|---|
| 1 | 90 |
| 2 | 120 |
| 3 | 120 |
| 4 | 180 |
| 5 | 180 |
| 6 | 200 |
| 7 | 200 |

After reaching the steady state, an average of 566 g/hr of a product containing 97% of tetrachloroethylene-bis-isocyanide dichloride was obtained. This result corresponded to a product yield of 91% relative to the starting material N,N-dimethylaminoacetonitrile.

EXAMPLE 4

This example shows that the first chlorination stage can also be carried out in other reactors than a bubble column.

100 g/hr of N,N-dimethylaminoacetonitrile and 850 g/hr of chlorine were passed, at 110° C., into 600 g of a mixture of chlorinated N-methyl-imidazoles and -imidazolines prepared in accordance with the process described in Example 1 and contained in a 5 liter glass vessel equipped with a stirrer, gas and liquid inlet tube, thermometer and gas outlet through a reflux condenser. The reaction volume was brought to 5 liters by means of a siphon tube and after reaching the appropriate level the excess product was siphoned off into a receiver and was stabilized therein by flushing out the chlorine.

2,560 g of the pale yellow product thus obtained, in which the proportion of isocyanide dichloride was less than 1%, were gassed in the installation according to FIG. 1 with 1,200 g/hr of chlorine, using the following temperature programs:

| Time/hr | Temperature/°C. |
|---|---|
| 5 | 120 |
| 5 | 140 |
| 5 | 160 |
| 5 | 180 |
| 10 | 210 |

2,730 g of product containing 97.5% of tetrachloroethylene-bis-isocyanide dichloride were obtained.

It will be appreciated that the instant specification and examples are set forth by way of illustration and not limitation, and that various modifications and changes may be made without departing from the spirit and scope of the present invention.

What is claimed is:

1. In the preparation of chlorinated N-methyl-imidazoles and N-methyl-imidazolines of the formula

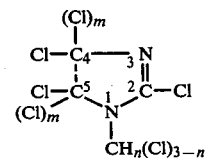

in which
n represents the number 0, 1, 2 or 3 and
m represents the number 0 or 1, a double bond being present between the C atoms in the 4-position and 5-position when m is 0, and a single bond being present when m is 1, by chlorinating N,N-dimethylaminoacetonitrile of the formula $(CH_3)_2N-CH_2-CN$ or its hydrochloride, the improvement which comprises introducing N,N-dimethyl-aminoacetonitrile or its hydrochloride into a mixture of its chlorination products, with simultaneous addition of chlorine gas, in the absence of a solvent, at a temperature from about 70° to 150° C.

2. A process according to claim 1, wherein chlorination is carried out at a temperature from about 90° to 130° C.

3. A process according to claim 1, wherein chlorination is carried out in a bubble column reactor or in a stirred kettle.

4. A process according to claim 1, wherein chlorination is carried out in a bubble column reactor with the gas and liquid flowing counter-current.

* * * * *